US00PP32252P3

(12) United States Plant Patent
Hartman

(10) Patent No.: US PP32,252 P3
(45) Date of Patent: Sep. 29, 2020

(54) ***CALADIUM* PLANT NAMED 'CLOWNING AROUND'**

(50) Latin Name: ***Caladium* X *hortulanum***
Varietal Denomination: Clowning Around

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/501,041

(22) Filed: Feb. 13, 2019

(65) Prior Publication Data

US 2020/0260626 P1 Aug. 13, 2020

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/00
See application file for complete search history.

*Primary Examiner* — Anne Marie Grunberg
(74) *Attorney, Agent, or Firm* — C. A. Whealy

(57) ABSTRACT

A new and distinct cultivar of *Caladium* plant named 'Clowning Around', characterized by its intermediate to tall height; upright and mounding plant habit; dense and bushy appearance; vigorous growth habit and rapid growth rate; fancy-type leaves that have dark green-colored margins with greyed red, greyed purple and red-colored centers with random dark green-colored spots and blotches; and leaf petioles that are medium green flushed with greyed red in color with dark greenish brown-colored stippling, streaks and tessellations.

5 Drawing Sheets

Figure 1:
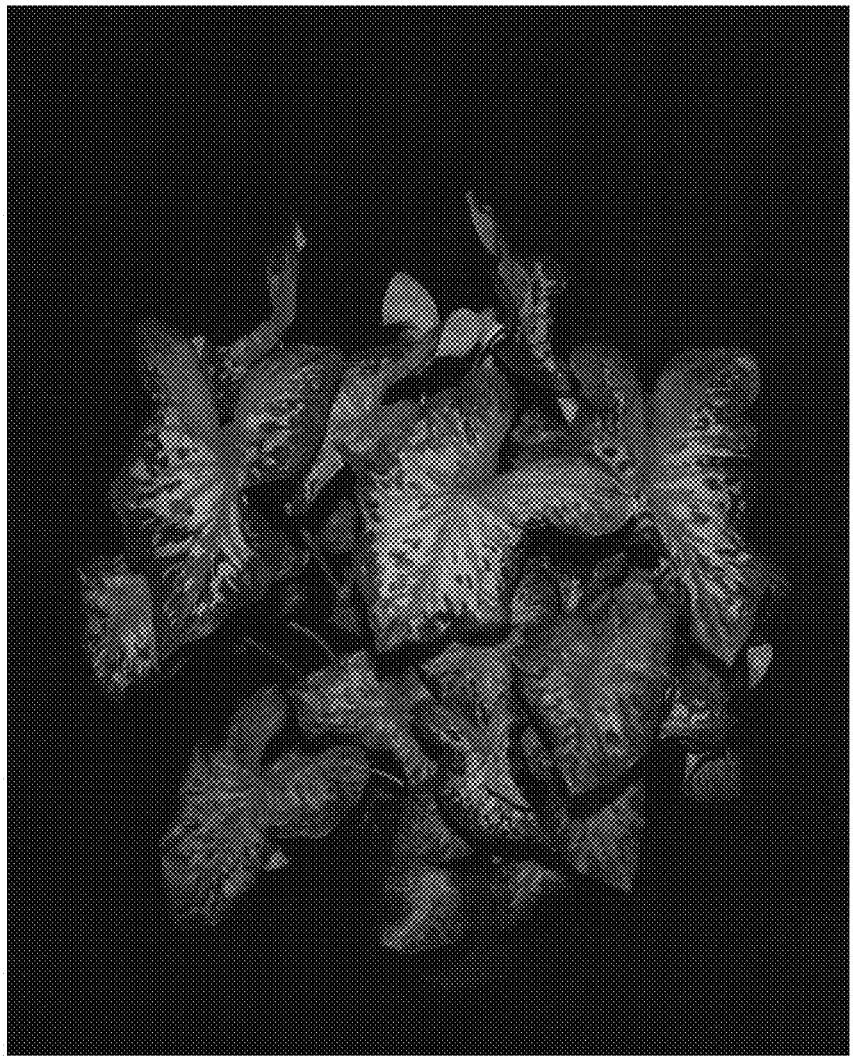

Botanical designation: *Caladium* X *hortulanum.*
Cultivar denomination: 'CLOWNING AROUND'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'Clowning Around'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2012 in Avon Park, Fla. of *Caladium* X *hortulanum* 'Red Flash', not patented, as the female, or seed, parent with *Caladium* X *hortulanum* 'Twist N' Shout', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2013.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2014 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Clowning Around'. These characteristics in combination distinguish 'Clowning Around' as a new and distinct *Caladium* plant:

1. Intermediate to tall in height and upright and mounding plant habit; dense and bushy appearance.
2. Vigorous growth habit and rapid growth rate.
3. Fancy-type leaves that have dark green-colored margins with greyed red, greyed purple and red-colored centers with random dark green-colored spots and blotches.
4. Petioles that are medium green flushed with greyed red in color with dark greenish brown-colored stippling, streaks and tessellations.

Plants of the new *Caladium* differ primarily from plants of the female parent, 'Red Flash', in the following characteristics:

1. Plants of the new *Caladium* grow much faster than plants of 'Red Flash'.
2. Plants of the new *Caladium* and 'Red Flash' differ in leaf color as leaves of plants of the new *Caladium* have dark green-colored margins with greyed red, greyed purple and red-colored centers with random dark green-colored spots and blotches whereas leaves of plants of 'Red Flash' have red-colored venation and interveinal areas with pink and white-colored spots and dark green-colored borders.

Plants of the new *Caladium* differ primarily from plants of the male parent, 'Twist N' Shout', in leaf color as leaves of plants of the new *Caladium* have dark green-colored margins with greyed red, greyed purple and red-colored centers with random dark green-colored spots and blotches whereas leaves of plants of 'Twist N' Shout' are olive green in color with green to coppery bronze-colored venation and coppery orange-colored spots and blotches.

Plants of the new *Caladium* can be compared to plants of *Caladium* X *hortulanum* 'Creamsickle', disclosed in U.S. Plant Pat. No. 23,991. In side-by-side comparisons, plants of the new *Caladium* differ primarily from plants of 'Creamsickle' in leaf color as leaves of plants of the new *Caladium* have dark green-colored margins with greyed red, greyed purple and red-colored centers with random dark green-colored spots and blotches whereas leaves of plants of 'Creamsickle' have greyed green-colored venation, greyed green and greyed purple-colored interveinal areas interspersed with dark green-colored sectors and borders.

Plants of the new *Caladium* can be compared to plants of *Caladium* X *hortulanum* 'Mesmerized', disclosed in U.S. Plant Pat. No. 29,545. In side-by-side comparisons, plants of the new *Caladium* differ primarily from plants of 'Mesmerized' in leaf color as leaves of plants of the new *Caladium* have dark green-colored margins with greyed red, greyed purple and red-colored centers with random dark green-colored spots and blotches whereas leaves of plants of 'Mesmerized' are variegated with variable areas that are dark green, red orange, whitish green and white in color; with development, mature leaves are mostly dark green in color with variable areas of variegation and interveinal areas with variably coalescing red orange-colored spots and splotches.

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1 of 7) is a side perspective view of a typical plant of 'Clowning Around' in a container and grown in a shadehouse (tuber de-eyed).

Figure 2:
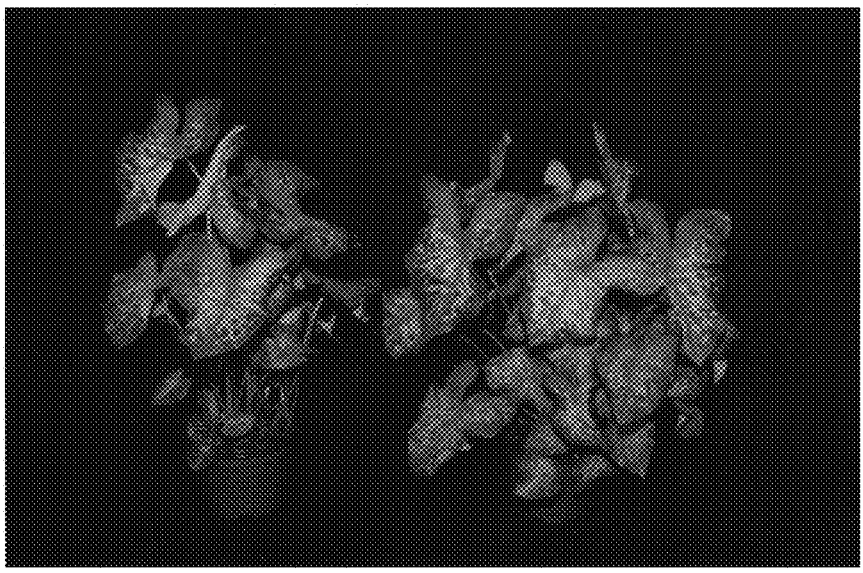

The photograph at the top of the second sheet (FIG. 2 of 7) is a comparison view of typical plants of 'Clowning Around' grown in containers; the plant on the left has not had its tuber de-eyed and the plant on the right has had its tuber de-eyed prior to planting.

Figure 3:
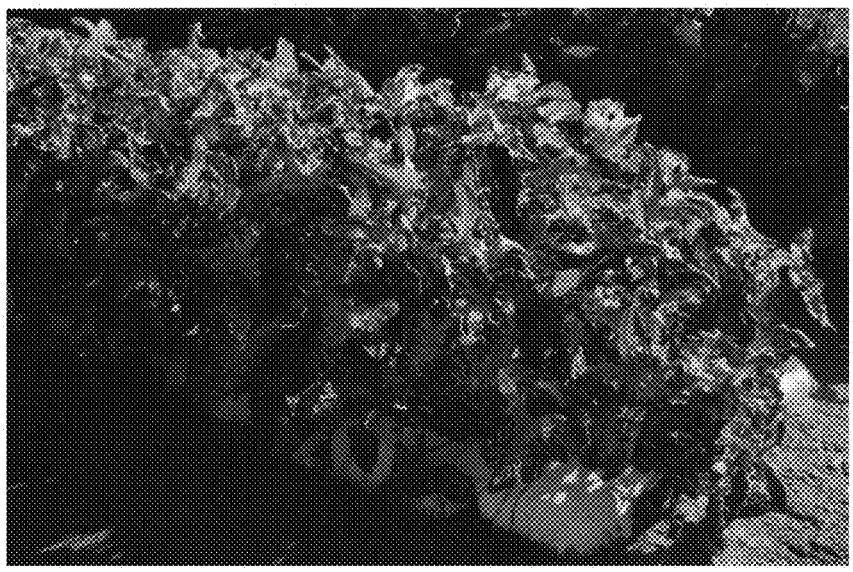

The photograph at the bottom of the second sheet (FIG. 3 of 7) is a side perspective view of typical plants of 'Clowning Around' grown in an open production field.

Figure 4:
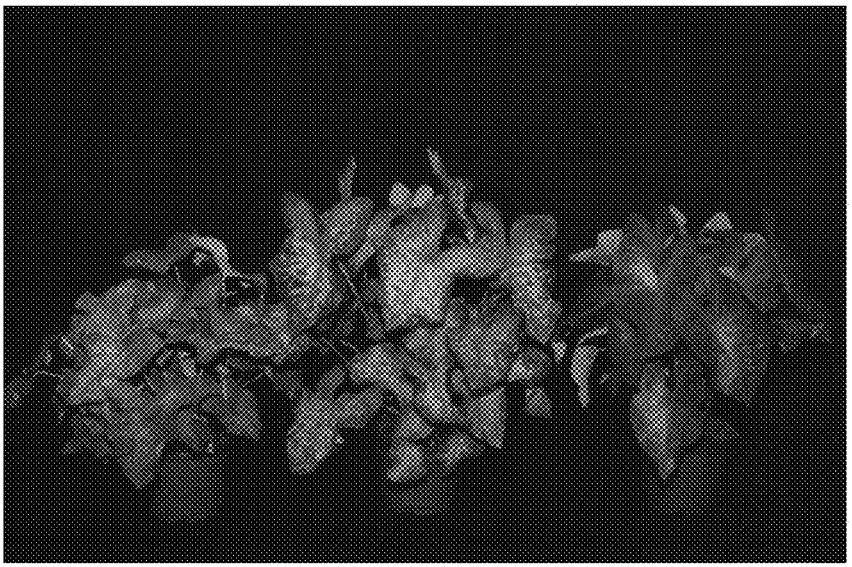

The photograph at the top of the third sheet (FIG. 4 of 7) is a comparison view of typical potted plants of the female parent, 'Red Flash' (right), 'Clowning Around' (center) and the male parent, 'Twist N' Shout' (left).

Figure 5:
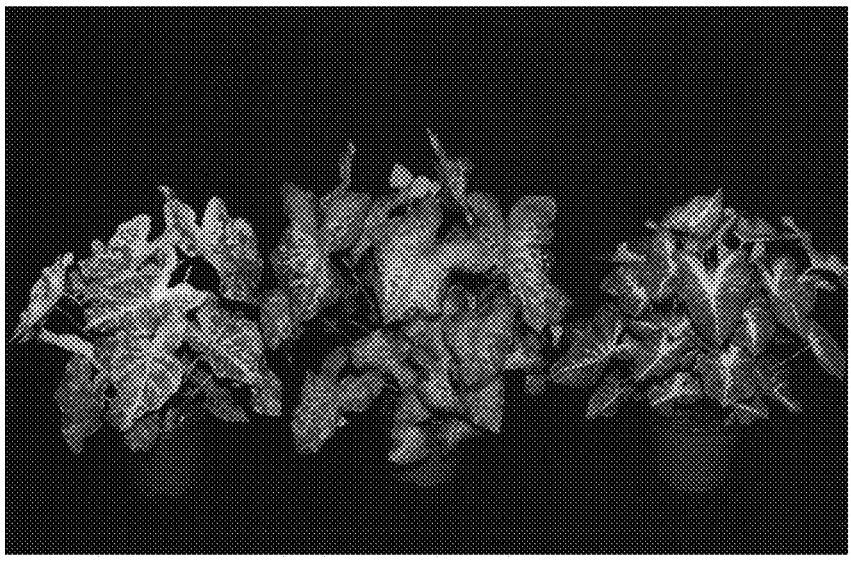

The photograph at the bottom of the third sheet (FIG. 5 of 7) is a comparison view of typical potted plants of 'Mesmerized' (left), 'Clowning Around' (center) and 'Creamsickle' (right).

Figure 6:
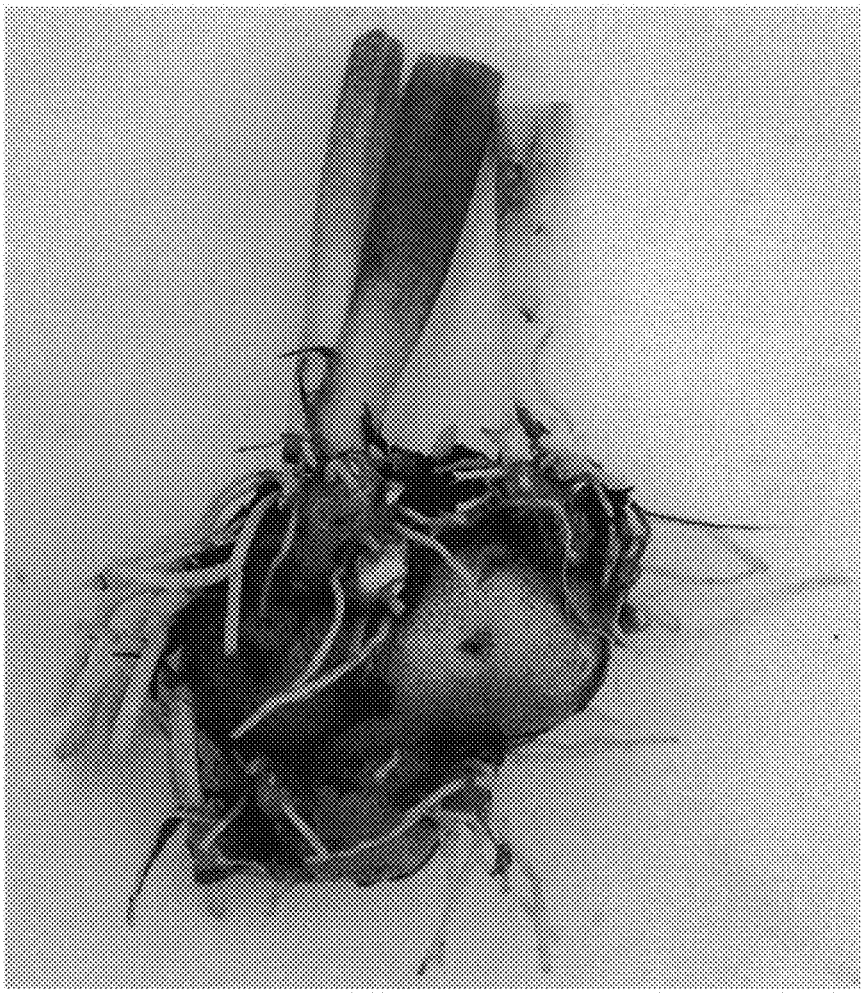

The photograph on the fourth sheet (FIG. 6 of 7) is a close-up view of typical freshly-harvested tubers with roots and leaf petioles of 'Clowning Around'.

Figure 7:
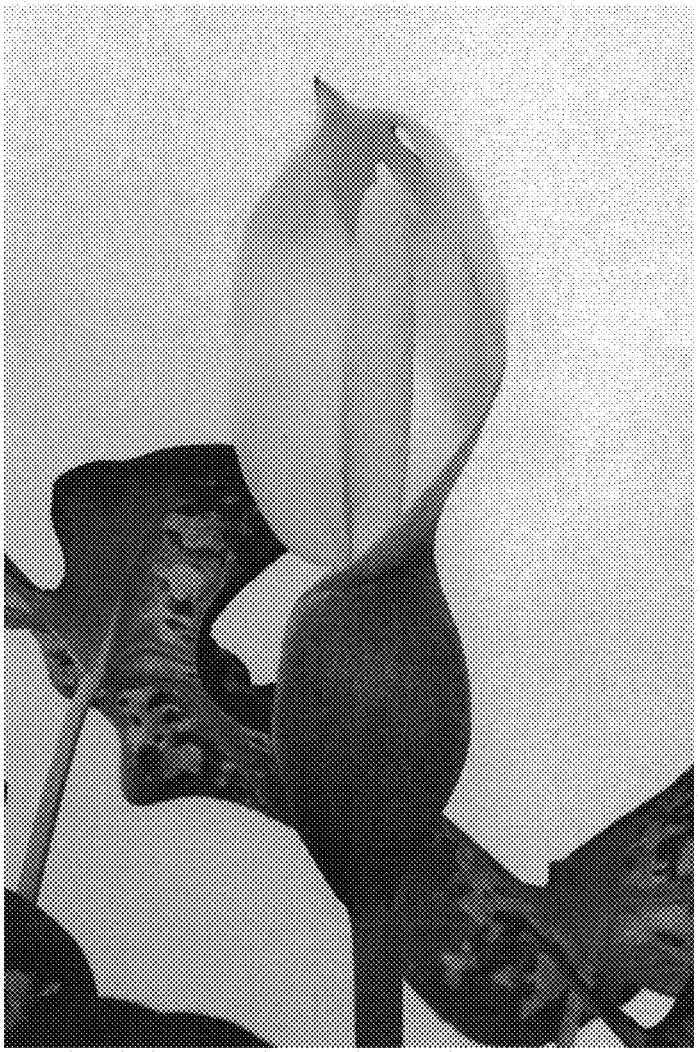

The photograph on the fifth sheet (FIG. 7 of 7) is a close-up view of a typical inflorescence of 'Clowning Around'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shadehouse were eight weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'Clowning Around'.

Parentage:

*Female, or seed, parent.*—*Caladium* X *hortulanum* 'Red Flash', not patented.

*Male, or pollen, parent.*—*Caladium* X *hortulanum* 'Twist N' Shout', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments elliptic and irregular in shape. Height: About 3.7 cm. Diameter: About 4.8 cm to 7.2 cm. Segment height: About 1.9 cm to 2.5 cm. Segment diameter: About 1.6 cm to 2.2 cm. Axillary bud size: About 3.5 mm by 5 mm. Texture: Thick, starchy; somewhat brittle. Color: Epidermis, freshly-harvested: Close to 155B. Epidermis, dried: Close to 200A. Cortical tissue: Close to 2D. Axillary buds: Close to 38D. Root description: Thick, fleshy contractile roots with few lateral branches; color, close to N155D. Rooting habit: Sparse.

Plant description:

*Plant type.*—Herbaceous perennial; suitable as a potted plant in containers 15-cm to 25-cm and suitable as a landscape plant in shaded areas.

*Plant and growth habit.*—Intermediate to tall in height and upright to mounded plant habit; inverted triangle and wider than tall; dense and bushy appearance; vigorous growth habit and rapid growth rate; potted plants finish in saleable form in about six to seven weeks after planting tubers; leaf petioles and leaves arise from one or more growing points on tubers; leaf petioles initially upright and outwardly leaning with development.

*Plant height, from soil level to top of foliar plane, shadehouse-grown potted plants.*—About 29 cm to 37 cm.

*Plant height, from soil level to top of inflorescences, shadehouse-grown potted plants.*—About 35.5 cm.

*Plant diameter or spread, shadehouse-grown potted plants*.—About 42 cm to 44 cm.

*Number of shoots per plant, shadehouse-grown potted plants, tubers not de-eyed*.—About three to four develop per #1 tuber.

*Number of shoots per plant, shadehouse-grown potted plants, tubers de-eyed*.—About five to six develop per #1 tuber.

*Cataphylls, shadehouse-grown potted plants*.—Length: About 6.8 cm. Width: About 1.2 cm. Shape: Narrowly elliptic. Apex: Acuminate. Base: Sheathing the stem. Color, inner surface: Close to N155C and 194D faintly tinged with close to 181D; colors and patterns on the outer surface are visible on the inner surface. Color, outer surface: Close to 147B to 147C sparsely streaked and stippled with close to 147B tinged with 200A; with development, color becoming closer to 199C and 200C.

Leaf description:

*Arrangement and type*.—Alternate; simple; fancy-type.

*Length, shadehouse-grown potted plants*.—About 16 cm to 22 cm.

*Width, shadehouse-grown potted plants*.—About 15 cm to 17 cm; when flattened, about 15.5 cm to 18 cm.

*Shape*.—Ovate.

*Apex*.—Acute or cuspidate.

*Base*.—Sagittate, peltate to hastate.

*Margin*.—Entire; undulate with broad undulations.

*Texture and luster, upper surface*.—Rugose, glabrous; dull.

*Texture and luster, lower surface*.—Rugose, glabrous; center and venation, glaucous; dull sheen.

*Venation pattern*.—Pinnate.

*Color, shadehouse-grown potted plants*.—Developing and fully developed leaves, upper surface: Background color: Close to 147A. Leaf edge: Close to 187A and 185A. Basal notch: Close to 187B. Midvein: Close to 53B; areas surrounding midvein, close to 182A and 50B. Primary veins: Close to 53B to 53C; areas surrounding primary veins, close to 182A and 50B. Interveinal areas: Distally, close to 179B, 179C or 179D, may or not be tinged with 147B; proximally, close to 185A, 184A and 53B to 53C. Random spots and blotches: Close to 147A tinged with 139A. Developing and fully developed leaves, lower surface: Background color: Close to 189A tinged with 191A and 191A. Leaf edge: Close to 187A and 185A. Basal notch: Close to 187A. Midvein: Close to 60A and 184B; areas surrounding midvein, close to 184B tinged with 60A. Primary venation: Close to 182C and 184B to 184C; areas surrounding primary venation, close to 184B tinged with 60A. Interveinal areas: Close to N170D to N170D. Random spots and blotches: Close to 191A and 189A tinged with 191A.

*Petioles*.—Aspect: Initially upright and straight and outwardly leaning with development; flexible. Length, shadehouse-grown potted plants: About 16 cm to 27.5 cm. Diameter, distally, shadehouse-grown potted plants: About 4 mm to 6 mm. Diameter, proximally, shadehouse-grown potted plants: About 7 mm to 9 mm. Texture and luster: Smooth, glabrous; slightly glossy; just below leaf junction, glaucous. Color, shadehouse-grown potted plants, when developing and fully developed: Close to 147B, 147C and 146C randomly flushed with 182D and faintly stippled, streaked and tessellated with close to 147B and 147B tinged with 200A; distally (just below leaf junction), close to 182D and 147C to 147D. Wing length, shadehouse-grown potted plants: About 4 cm to 7 cm. Wing diameter, shadehouse-grown potted plants: About 6 mm to 9 mm. Texture and luster, inner and outer surfaces: Smooth, glabrous; dull. Wing color, shadehouse-grown potted plants: Inner surface: Close to 155C and 194D faintly tinged with 181D; colors and patterns on the outer surface are visible on the inner surface. Outer surface: Close to 147B and 147C sparsely stippled and streaked with 147B tinged with 200A.

Inflorescence description: Inflorescences observed on eight week-old shadehouse-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with mint and camphor notes.

*Natural flowering season and flower longevity*.—Plants of the new *Caladium* typically flower during the spring in central Florida; flowers develop about eight weeks after growth commences; inflorescences last about three days before fading; inflorescences persistent.

*Spathe*.—Length, overall: About 11.2 cm. Length, distal open portion: About 6.7 cm. Length, proximal closed portion: About 4.5 cm. Width, distal open portion: About 5.1 cm. Depth, distal open portion: About 2.4 cm. Width, at constriction: About 1.3 cm. Width, proximal closed portion: About 2.8 cm. Shape, open portion: Elliptic. Apex: Acuminate. Base: Acute. Margin: Entire; smooth; slightly recurved. Texture and luster, front surface: Smooth, glabrous; dull. Texture and luster, rear surface: Smooth, glabrous; dull; proximally, glaucous. Color, front surface: Distal open portion: Close to 155C with sparse fine speckles, close to 187B; with development, color becoming closer to 199B to 199C. Proximal closed portion: Close to 148C; towards the base, flushed with close to 187A; color does not change with development. Color, rear surface: Distal open portion: Close to 145D; towards the margins, close to 155C; color does not change with development. Proximal closed portion: Close to 183C with random areas of 147C tinged with 146C, streaked and mottled with close to 147C; color does not change with development.

*Spadix*.—Length, overall: About 8.8 cm. Length, male flower zone: About 4.9 cm. Length, sterile zone: About 2 cm. Length, female flower zone: About 1.9 cm. Diameter, male flower zone: About 9 mm. Diameter, sterile flower zone: About 5.5 mm. Diameter, female flower zone: About 8 mm. Shape: Columnar, spindle-shaped. Apex: Acute. Base:

Obtuse. Aspect: Upright. Color, mature, male zone: Close to 155D tinged with 150D. Color, mature, sterile zone: Close to 155B. Color, mature, female zone: Close to 158A. Male flowers: Quantity per spadix: About 105. Shape: Obovate. Height: About 3.2 mm. Diameter: About 3.8 mm. Pollen amount: Abundant. Pollen color: Close to 10C. Female flowers: Quantity per spadix: About 102. Shape: Obovate. Height: About 2 mm. Diameter: About 2.8 mm. Stigma color: Close to 158A. Ovary color: Close to 159C.

*Scape*.—Length: About 24.3 cm. Diameter: About 7 mm. Strength: Sturdy; flexible. Aspect: Mostly erect. Texture and luster: Smooth, glabrous; dull; distally, slightly glaucous. Color: Close to 147B tinged with 146B; faintly stippled and streaked with close to 200A; distally, close to 147B tinged with 182D.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'Clowning Around' as illustrated and described.

* * * * *